(12) United States Patent (10) Patent No.: US 12,667,419 B2
Song et al. (45) Date of Patent: Jun. 30, 2026

(54) METHOD AND APPARATUS FOR CONCENTRATING RADIO WAVE ENERGY CONSIDERING BREATHING AND LOCATION OF SUBJECT

(71) Applicant: ELECTRONICS AND TELECOMMUNICATIONS RESEARCH INSTITUTE, Daejeon (KR)

(72) Inventors: Won Young Song, Sejong-si (KR); Kwang Jae Lee, Daejeon (KR); Soon Ik Jeon, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 209 days.

(21) Appl. No.: 18/736,929

(22) Filed: Jun. 7, 2024

(65) Prior Publication Data

US 2024/0407843 A1 Dec. 12, 2024

(30) Foreign Application Priority Data

Jun. 7, 2023 (KR) ........................ 10-2023-0072946

(51) Int. Cl.
*A61B 18/18* (2006.01)
(52) U.S. Cl.
CPC .................................. *A61B 18/18* (2013.01)

(58) Field of Classification Search
CPC ...................................................... A61B 18/18
See application file for complete search history.

(56) References Cited

U.S. PATENT DOCUMENTS

| | | | |
|---|---|---|---|
| 9,504,850 B2 | 11/2016 | Zhang et al. | |
| 2005/0187464 A1* | 8/2005 | Ho ......................... | A61B 5/055 |
| | | | 600/428 |
| 2022/0080215 A1 | 3/2022 | Ko | |
| 2022/0395707 A1* | 12/2022 | Laurence, Jr. ......... | A61B 34/10 |

FOREIGN PATENT DOCUMENTS

| | | |
|---|---|---|
| KR | 10-2020-0083838 A | 7/2020 |
| KR | 10-2486572 B1 | 1/2023 |

* cited by examiner

*Primary Examiner* — Scott Luan

(57) ABSTRACT

A method and an apparatus for focusing radio wave energy are disclosed. According to an embodiment of a present disclosure, a method for focusing radio wave energy includes obtaining one or more internal tomographic images of a subject. The method also includes converting the one or more internal tomographic images into one or more numerical models. The method also includes calculating one or more first focusing parameters. The method also includes obtaining an image of the subject by monitoring the subject. The method also includes determining whether a second focusing parameter exists among the one or more first focusing parameters. The method also includes determining a final focusing parameter. The method also includes irradiating a lesion existing inside the subject with the radio wave energy using the final focusing parameter.

20 Claims, 20 Drawing Sheets

Phase of focusing parameter

*FIG. 3C*

METHOD AND APPARATUS FOR CONCENTRATING RADIO WAVE ENERGY CONSIDERING BREATHING AND LOCATION OF SUBJECT

CROSS-REFERENCE TO RELATED APPLICATIONS

The present application is based on, and claims priority from, Korean Patent Application Number 10-2023-0072946, filed Jun. 7, 2023, the disclosure of which is incorporated by reference herein in its entirety.

TECHNICAL FIELD

The present disclosure relates to a method and apparatus for focusing radio wave energy by taking into account the breathing and position of a subject. More specifically, the present disclosure relates to a method and apparatus for adjusting focusing parameters based on the breathing and position of a subject and focusing radio wave energy on the subject using the adjusted focusing parameters.

BACKGROUND

The contents described below merely provide background information related to the present disclosure and do not constitute prior art.

Incurable diseases, including cancer diseases, and degenerative musculoskeletal diseases are generally treated through invasive treatments using open surgery. Since invasive treatments are based on surgical treatment, they cause pain, physical burden, and aftereffects not only to elderly patients but also to general patients. Accordingly, noninvasive treatments that treat lesions inside the living body by irradiating the lesions inside the living body with high-density energy from outside the living body are attracting attention.

Non-invasive treatments are divided into radiation therapy and ultrasound therapy depending on the type of energy delivered to the lesion. In the case of radiation therapy, there is a problem of radiation exposure, and in the case of ultrasound therapy, there is a problem of limitations such as bone or air structures. Accordingly, treatment using radio wave energy that is safe and not limited by structures is being studied. Treatment technology using radio wave energy is a technology that treats lesions by irradiating a target with radio waves having a controlled magnitude and phase from outside the living body, focusing the radio wave energy, and increasing the temperature of the lesions with the radio wave energy.

In the treatment technology using radio wave energy, the living body is modeled as a model capable of being analyzed with electromagnetic analysis, and the magnitude and phase of radio waves are adjusted using such a model. The increase in temperature through radio wave energy transfer does not occur in a short period of time, and requires time. If the position of the living body changes during treatment using radio wave energy, the living body expands or contracts due to breathing, or the lesion moves up or down, problems may arise where the radio wave energy is focused on the wrong area. To address this problem, it is necessary to monitor the living body and readjust the magnitude and phase of radio waves by considering the breathing and position of the living body.

SUMMARY

In view of the above, the present disclosure provides a method and an apparatus for focusing radio wave energy capable of adjusting focusing parameters in consideration of the breathing and position of a subject.

In addition, according to one embodiment, the present disclosure provides a method and an apparatus for focusing radio wave energy capable of continuously focusing radio wave energy on the lesion even when the subject breathes and the position of the subject changes.

Further, according to one embodiment, the present disclosure provides a method and an apparatus for focusing radio wave energy in which treatment may not be stopped even when the subject breathes or the position of the subject changes.

Furthermore, according to one embodiment, the present disclosure provides a method and an apparatus for focusing radio wave energy capable of minimizing a patient's discomfort due to long-term treatment.

The objects to be achieved by the present disclosure are not limited to the objects mentioned above, and other objects not mentioned will be clearly understood by those skilled in the art from the description below.

According to the present disclosure, a method for focusing radio wave energy includes obtaining one or more internal tomographic images of a subject. The method also includes converting the one or more internal tomographic images into one or more numerical models. The method also includes calculating one or more first focusing parameters based on the one or more numerical models. The method also includes obtaining an image of the subject by monitoring the subject. The method also includes determining whether a second focusing parameter exists among the one or more first focusing parameters based on the image of the subject. The method also includes determining a final focusing parameter based on the determination result. The method also includes irradiating a lesion existing inside the subject with the radio wave energy using the final focusing parameter. and the radio wave energy is radiated through a plurality of antennas.

According to the present disclosure, an apparatus for predicting cyber threats includes a memory and a plurality of processors. At least one of the plurality of processors is configured to obtain one or more internal tomographic images of a subject. The at least one of the plurality of processors is also configured to convert the one or more internal tomographic images into one or more numerical models. The at least one of the plurality of processors is also configured to calculate one or more first focusing parameters based on the one or more numerical models. The at least one of the plurality of processors is also configured to obtain an image of the subject by monitoring the subject. The at least one of the plurality of processors is also configured to determine whether a second focusing parameter exists among the one or more first focusing parameters based on the image of the subject. The at least one of the plurality of processors is also configured to determine a final focusing parameter based on the determination result. The at least one of the plurality of processors is also configured to irradiate a lesion existing inside the subject with the radio wave energy to using the final focusing parameter. The radio wave energy is radiated through a plurality of antennas and the plurality of antennas are arranged in multiple layers.

According to the present disclosure, a computer-readable recording medium is a computer-readable recording medium storing instructions, the instructions, when executed by the computer, may cause the computer to perform obtaining one or more internal tomographic images of a subject. The instructions, when executed by the computer, may also cause the computer to perform converting the one or more internal tomographic images into one or more numerical models. The instructions, when executed by the computer, may also cause the computer to perform calculating one or more first focusing parameters based on the one or more numerical models. The instructions, when executed by the computer, may also cause the computer to perform obtaining an image of the subject by monitoring the subject. The instructions, when executed by the computer, may also cause the computer to perform determining whether a second focusing parameter exists among the one or more first focusing parameters based on the image of the subject. The instructions, when executed by the computer, may also cause the computer to perform determining a final focusing parameter based on the determination result. The instructions, when executed by the computer, may also cause the computer to perform irradiating a lesion existing inside the subject with the radio wave energy using the final focusing parameter According to the present disclosure, the focusing parameters can be adjusted in consideration of the breathing and position of a subject.

According to one embodiment of the present disclosure, the radio wave energy can be continuously focused on the lesion even when the subject breathes and the position of the subject changes.

According to one embodiment of the present disclosure, treatment may not be stopped even when the subject breathes or the position of the subject changes.

According to one embodiment of the present disclosure, it is possible to minimize a patient's discomfort due to long-term treatment.

The effects of the present disclosure are not limited to the effects mentioned above, and other effects not mentioned will be clearly understood by one of ordinary skill in the art from the following description.

BRIEF DESCRIPTION OF THE DRAWINGS

FIGS. 3A, 3B, and 3C are diagrams for explaining a power loss density according to the breathing of a subject and a phase of a focusing parameter without considering the breathing of the subject, according to one embodiment of the present disclosure.

DETAILED DESCRIPTION

Figure 1:
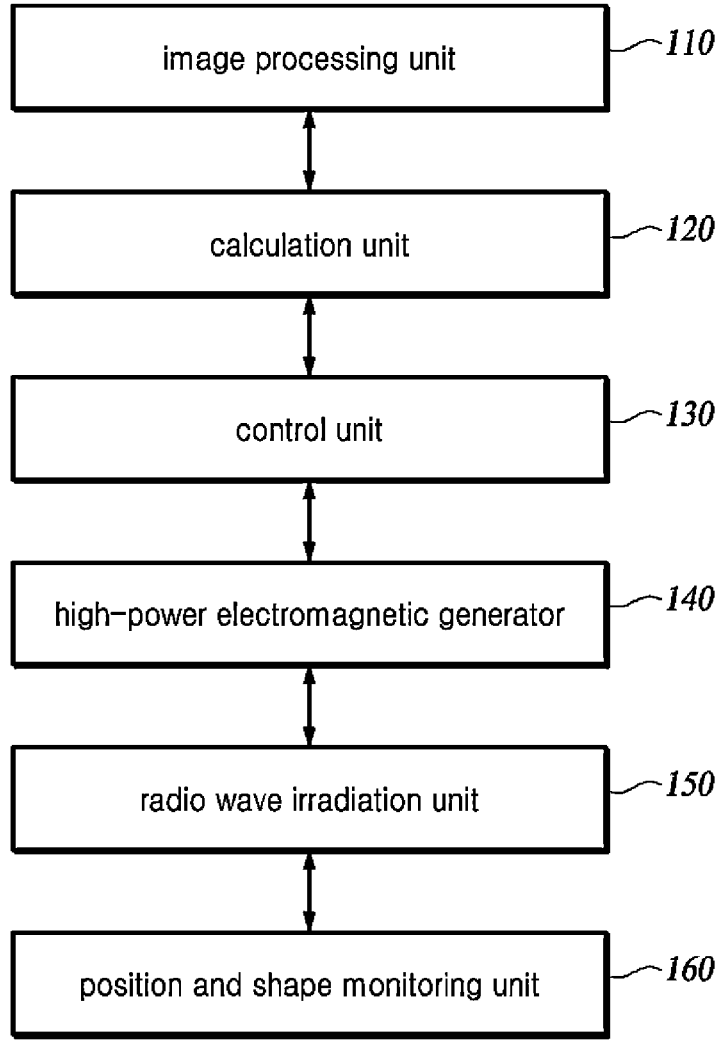
FIG. 1 is a block diagram for explaining a treatment system using radio wave energy according to one embodiment of the present disclosure.

Hereinafter, some exemplary embodiments of the present disclosure will be described in detail with reference to the accompanying drawings. In the following description, like reference numerals preferably designate like elements, although the elements are shown in different drawings. Further, in the following description of some embodiments, a detailed description of known functions and configurations incorporated therein will be omitted for the purpose of clarity and for brevity.

Additionally, various terms such as first, second, A, B, (a), (b), etc., are used solely to differentiate one component from the other but not to imply or suggest the substances, order, or sequence of the components. Throughout this specification, when a part 'includes' or 'comprises' a component, the part is meant to further include other components, not to exclude thereof unless specifically stated to the contrary. The terms such as 'unit', 'module', and the like refer to one or more units for processing at least one function or operation, which may be implemented by hardware, software, or a combination thereof.

The following detailed description, together with the accompanying drawings, is intended to describe exemplary embodiments of the present disclosure, and is not intended to represent the only embodiments in which the present disclosure may be practiced.

FIG. 1 is a block diagram for explaining a treatment system using radio wave energy according to one embodiment of the present disclosure.

Referring to FIG. 1, the treatment system using radio wave energy may include an image processing unit 110, a calculation unit 120, a control unit 130, a high-power electromagnetic generator 140, a radio wave irradiation unit 150, and a position and shape monitoring unit 160. The image processing unit 110 may load an internal tomography image of a subject. The internal tomographic image may correspond to a medical image. The internal tomography image may be loaded at regular time intervals depending on the subject's breathing. As an example, the subject may correspond to a living body. As an example, the internal tomographic image may correspond to any image that can be converted into a numerical model capable of being analyzed with electromagnetic analysis. The image processing unit 110 may convert the internal tomography image of the subject into a numerical model capable of being analyzed with electromagnetic analysis. The numerical model may include electromagnetic properties. The image processing unit 110 may transmit the numerical model to the calculation unit 120. The calculation unit 120 may calculate a focusing parameter using the numerical model. The focusing parameter may be used to irradiate a desired position within the subject with radio wave energy. The focusing parameter may be calculated for each time point of the breath.

The calculation unit 120 may transmit the focusing parameter to the control unit 130. The control unit 130 may transmit the focusing parameter to the high-power electromagnetic generator 140. The high-power electromagnetic generator 140 may generate electromagnetic waves using the focusing parameter. The radio wave irradiation unit 150 may irradiate the subject with the generated electromagnetic waves. The radio wave irradiation unit 150 may be comprised of a plurality of multi-layer antennas to take into account the up-down movement of the subject according to the subject's breathing. In the process of irradiating the subject with electromagnetic waves, the position and shape monitoring unit 160 may monitor the position and shape of the subject. For example, the position and shape monitoring unit 160 may include an MRI imaging device, an electromagnetic wave sensor, a laser sensor, or a piezoelectric sensor. The position and shape monitoring unit 160 may transmit the monitoring results to the control unit 130. The control unit 130 may check the monitoring results and select a pre-calculated focusing parameter, if any. The control unit 130 may check the monitoring result and, if there is no pre-calculated focusing parameter, transmit the monitoring results to the calculation unit 120.

The calculation unit 120 may recalculate the focusing parameter using the monitoring results. The calculation unit 120 may transmit the recalculated focusing parameter to the control unit 130. The control unit 130 may transmit the recalculated focusing parameter to the high-power electromagnetic generator 140. The high-power electromagnetic generator 140 may regenerate electromagnetic waves using the recalculated focusing parameter. The radio wave irradiation unit 150 may irradiate the subject with the regenerated electromagnetic waves.

Figure 2A:
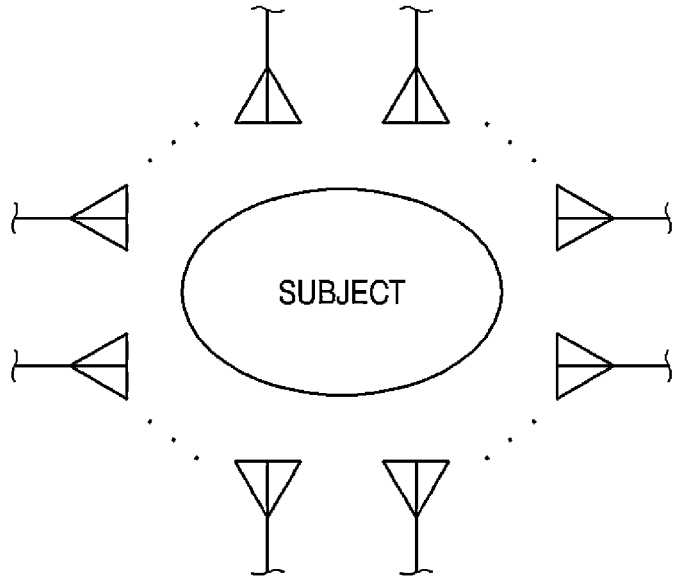
FIGS. 2A and 2B are diagrams for explaining a radio wave irradiation unit according to one embodiment of the present disclosure.
Figure 2B:
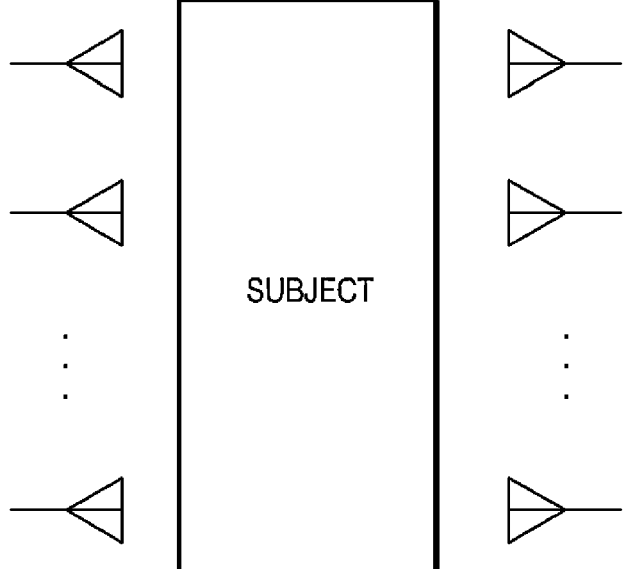

FIGS. 2A and 2B are diagrams for explaining the radio wave irradiation unit according to one embodiment of the present disclosure.

Referring to FIG. 2A, the radio wave radiation unit 150 may be comprised of a plurality of multi-layered antennas. The plurality of antennas may be arranged to surround the subject in a circle.

Referring to FIG. 2B, the radio wave radiation unit 150 may be comprised of a plurality of multi-layered antennas. A plurality of antennas may be arranged linearly on the left side of the subject. A plurality of antennas may be arranged linearly on the right side of the subject. When a real patient breathes, internal lesions may move up and down. As the internal lesion moves up and down, the position to focus the radio wave energy also needs to move up and down. Accordingly, the radio wave radiation unit 150 may be comprised of a plurality of multi-layered antennas.

Figure 3A:
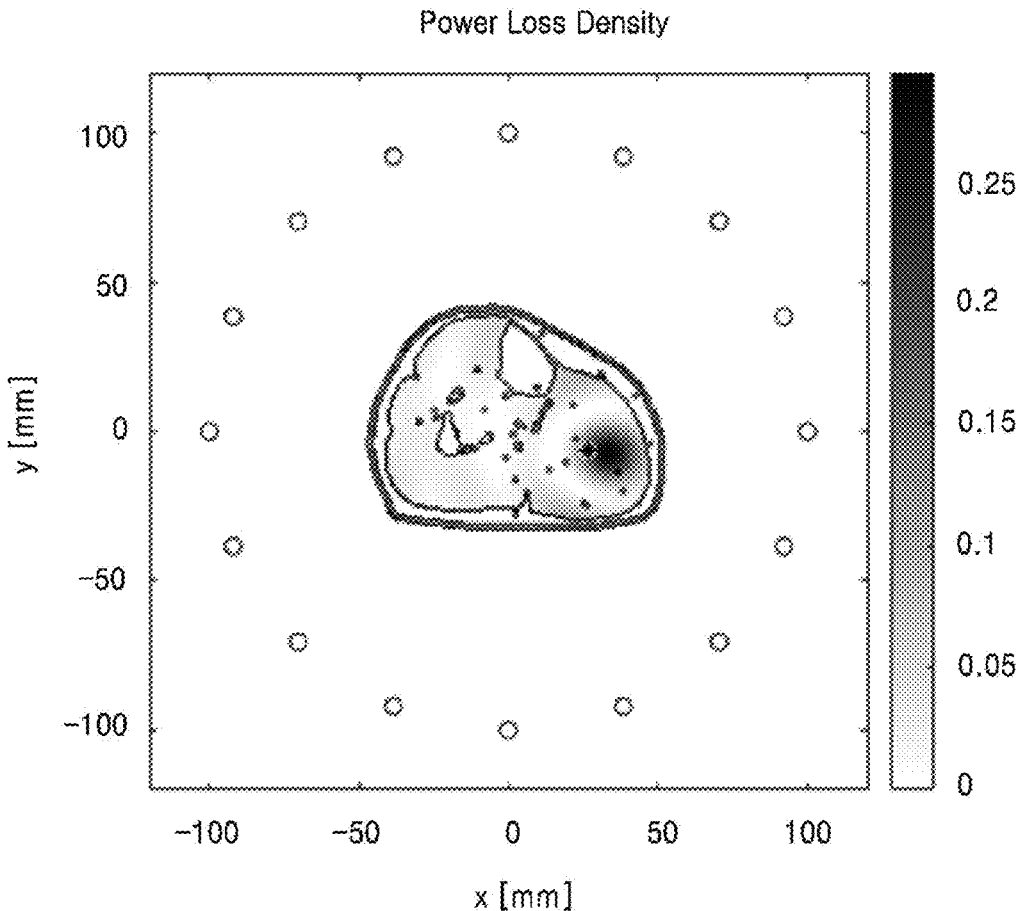
Figure 3B:
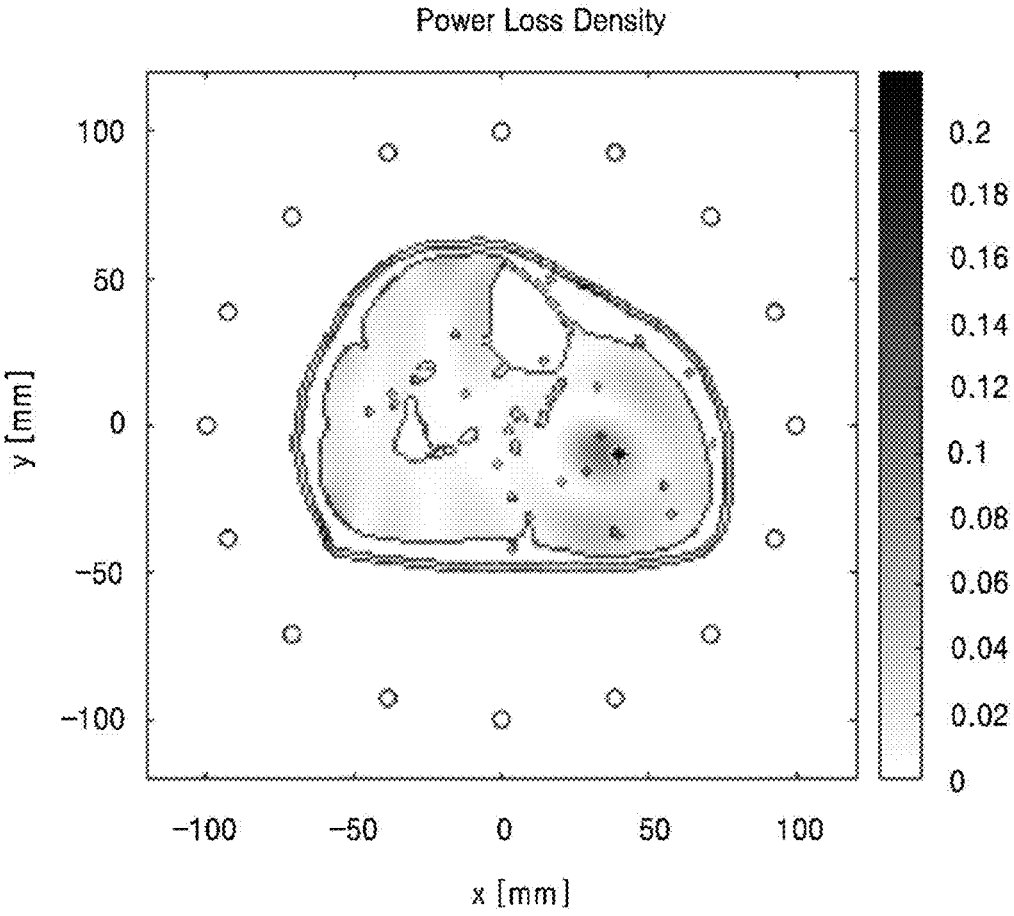
Figure 3C:
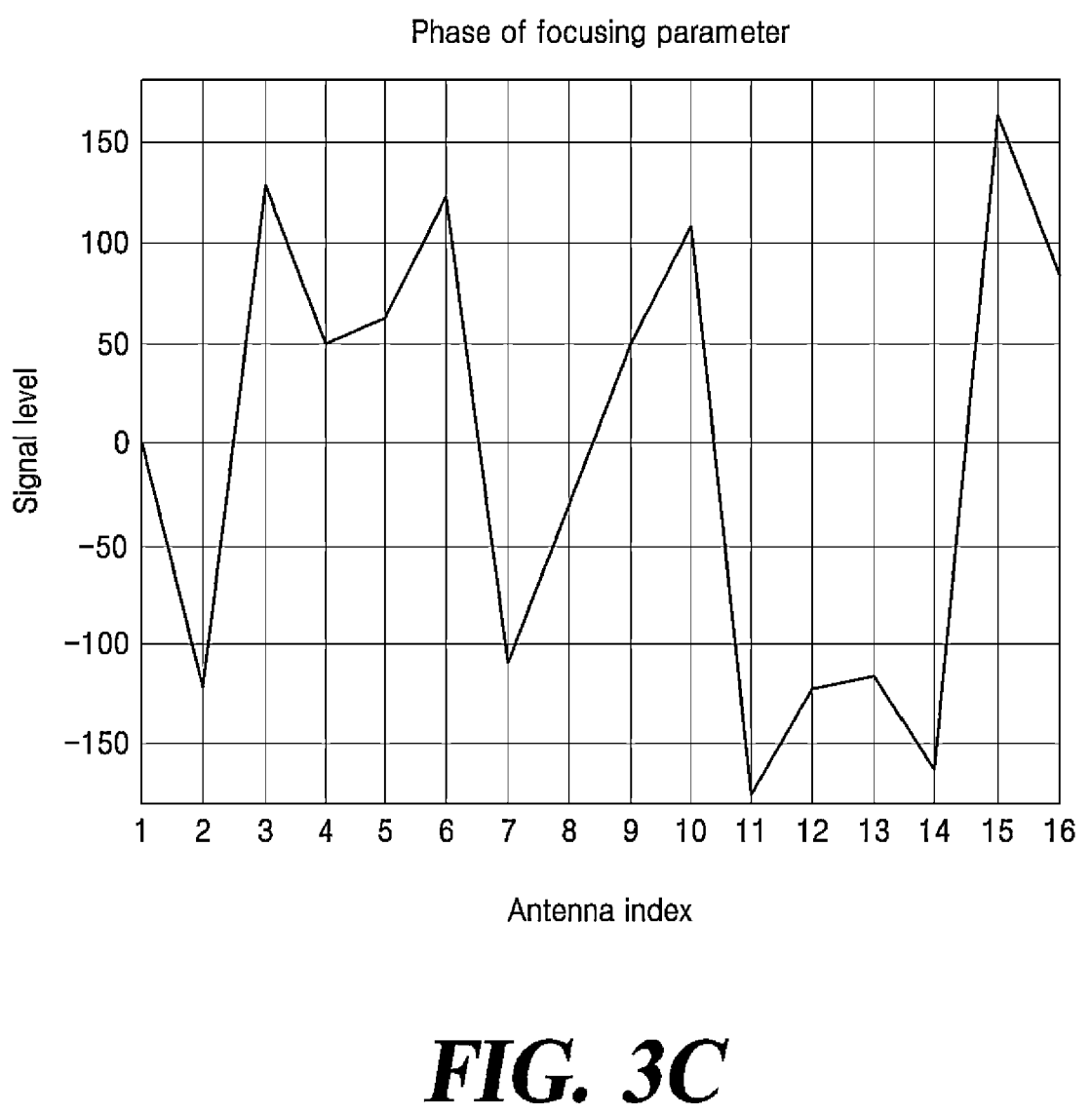

FIGS. 3A, 3B, and 3C are diagrams for explaining the power loss density according to the breathing of the subject and the phase of the focusing parameter without considering the breathing of the subject, according to one embodiment of the present disclosure.

FIG. 3A shows the power loss density of the subject when the subject is breathing and the time is $t_n$. The position of the subject is represented by the x-axis and y-axis in mm units. The power loss density for each position of the subject is displayed.

FIG. 3B shows the power loss density of the subject when the subject is breathing and the time is $t_{n+1}$. The position of the subject is represented by the x-axis and y-axis in mm units. The power loss density for each position of the subject is displayed. The subject expands due to the subject's breathing. The size of the subject at time $t_n$ is smaller than the size of the subject at time $t_{n+1}$.

FIG. 3C shows the phase of the focusing parameter. The phase of the focusing parameter is displayed for each antenna. There are 16 antennas and they are identified by an index. The phase of the focusing parameter corresponds to that represented without considering the subject's breathing.

FIGS. 4A, 4B, 4C, and 4D are diagrams for explaining the power loss density according to a change in the position of the subject and the phase of the focusing parameter without considering the change in the position of the subject, according to one embodiment of the present disclosure.

Figure 4A:
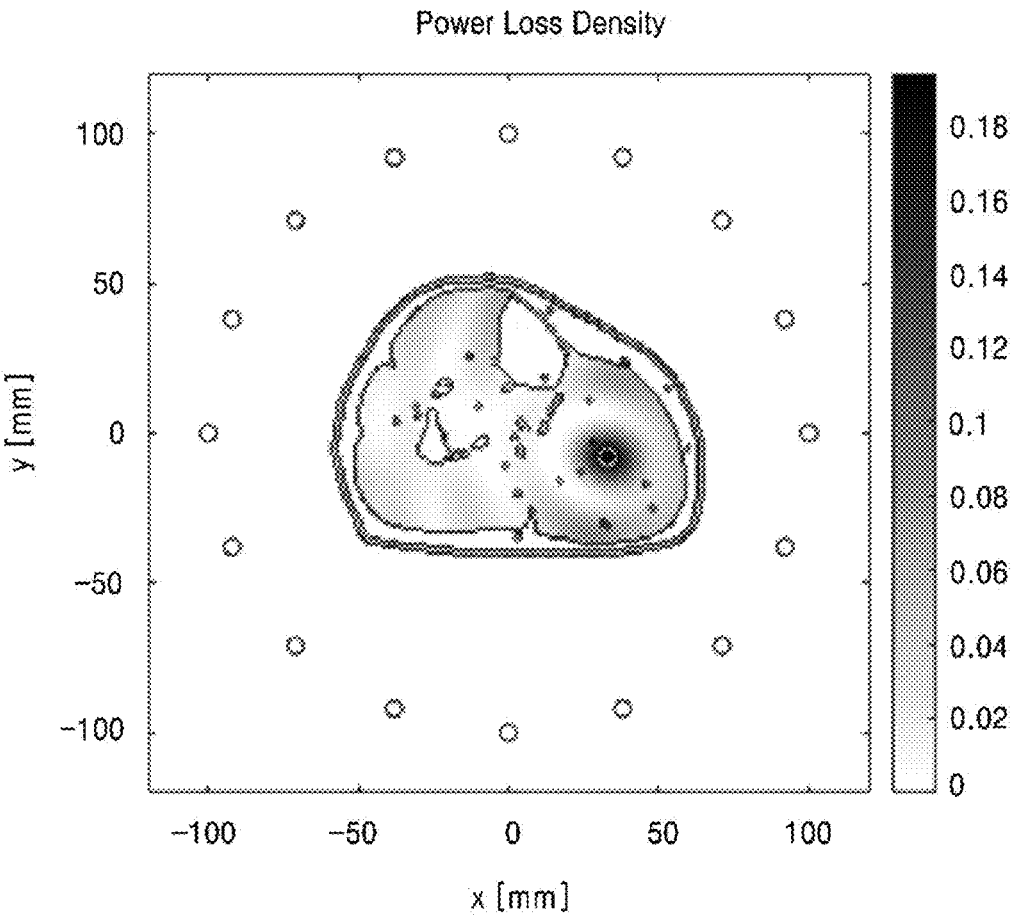
FIGS. 4A, 4B, 4C, and 4D are diagrams for explaining the power loss density according to a change in the position of a subject and a phase of a focusing parameter without considering the change in the position of the subject, according to one embodiment of the present disclosure.

FIG. 4A shows the power loss density of the subject in an initial state. The position of the subject is displayed by the x-axis and y-axis in mm units. The power loss density for each position of the subject is displayed.

Figure 4B:
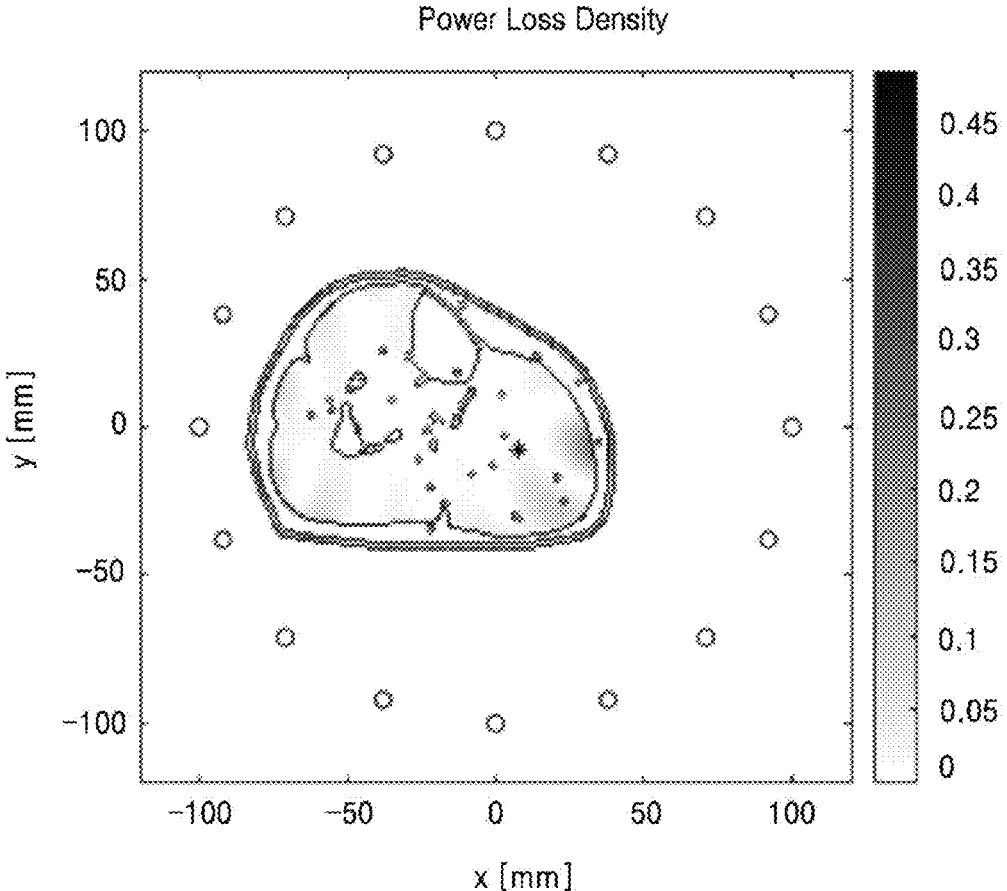

FIG. 4B shows the power loss density of the subject when the subject moves to the left from the initial state. The position of the subject is displayed by the x-axis and y-axis in mm units. The power loss density for each position of the subject is displayed.

Figure 4C:
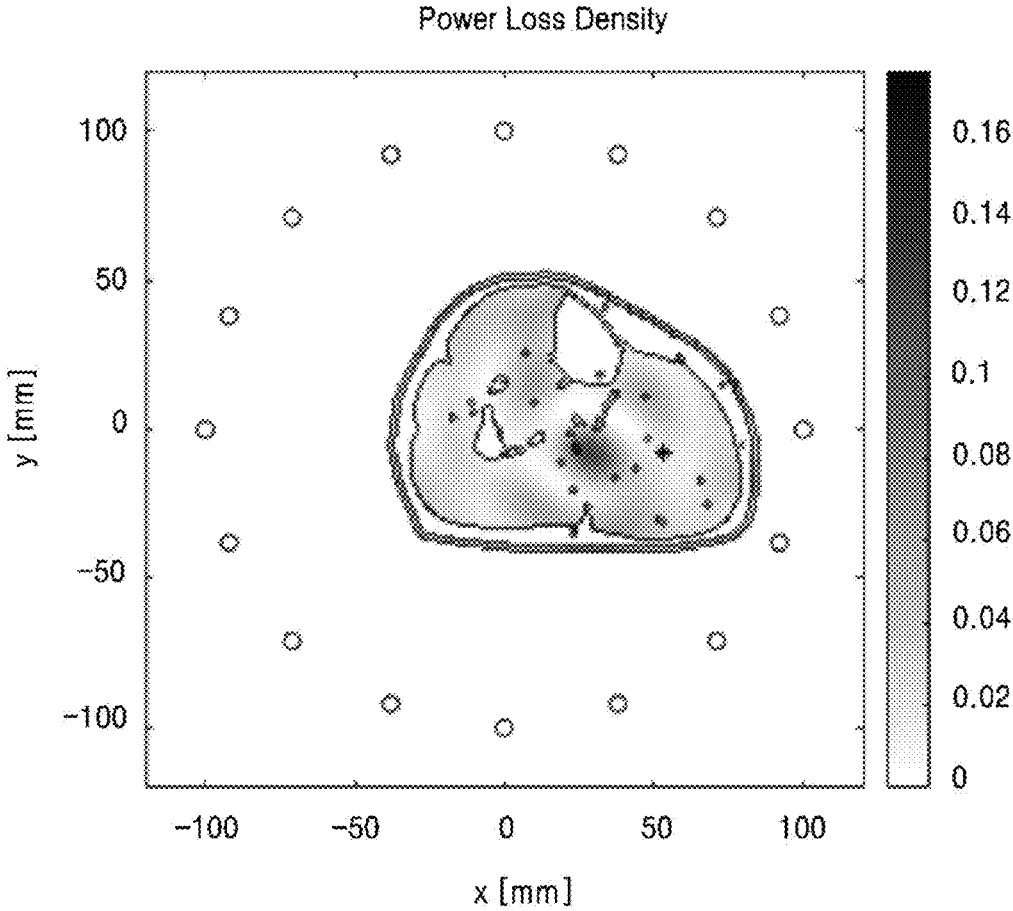

FIG. 4C shows the power loss density of the subject when the subject moves to the right from the initial state. The position of the subject is displayed by the x-axis and y-axis in mm units. The power loss density for each position of the subject is displayed.

Figure 4D:
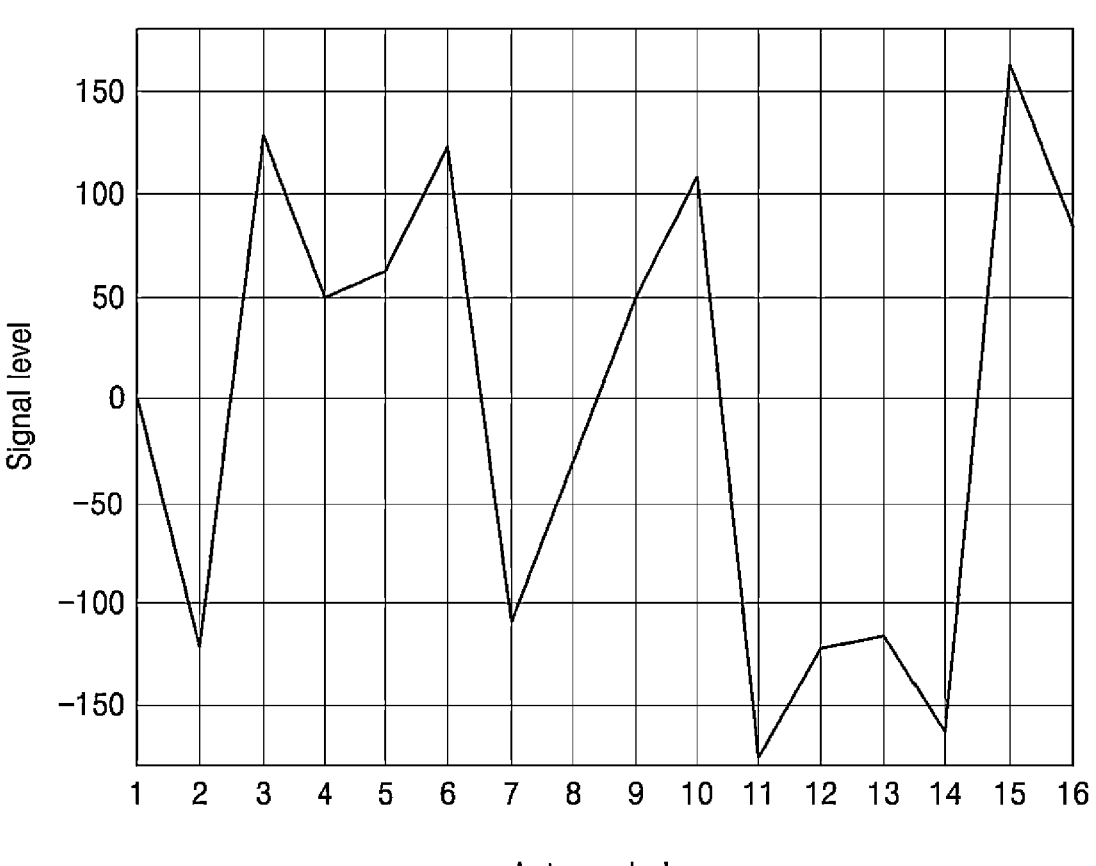

FIG. 4D shows the phase of the focusing parameter. The phase of the focusing parameter is displayed for each antenna. There are 16 antennas and they are identified by an index. The phase of the focusing parameter corresponds to that represented without considering the movement of the subject.

Figure 5:
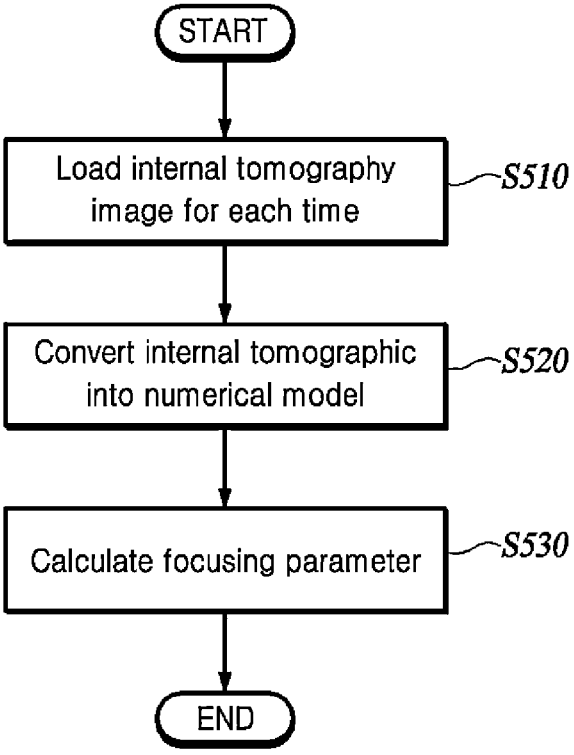
FIG. 5 is a diagram for explaining a process of calculating focus parameters before treatment, according to one embodiment of the present disclosure.

FIG. 5 is a diagram for explaining a process of calculating focus parameters before treatment, according to one embodiment of the present disclosure. The focusing parameter for each time may be calculated using internal tomography images for each time according to respiration before treatment. Instead of calculating the focusing parameter at every time, the focusing parameter may be calculated at specific time intervals.

Referring to FIG. 5, an internal tomography image for each time may be loaded (S510). The internal tomographic images by time may be loaded into the image processing unit. The internal tomography image may be loaded regular intervals divided by the respiratory cycle. The internal tomographic image may be converted into a numerical model capable of electromagnetic analysis (S520). The internal tomographic image may be converted into a numerical model capable of electromagnetic analysis in the image processing unit. The focusing parameter may be calculated using the numerical model (S530). A focusing parameter for focusing radio wave energy at a focusing target point rf may be calculated. K may correspond to multi-state data. K may be expressed as Equation 1.

$$K = g_{Rx}^T(r_f) g_{Tx}(r_f) \qquad \text{(Equation 1)}$$

K can be calculated as the product of the reception Green's function $g_{Rx}(rf)$ from rf to each antenna and the transmission Green's function $g_{Tx}(rf)$ from rf to each antenna. K can be decomposed into singular values as shown in Equation 2.

$$[U \quad S \quad V] = svd(K) \qquad \text{(Equation 2)}$$

Here, among the singular values, the first singular vector on the right may correspond to the focusing parameter as shown in Equation 3.

$$w_f = v_1 = [w_1 \quad w_2 \quad \cdots \quad w_N]^T \qquad \text{(Equation 3)}$$

The reception Green's function and the transmission Green's function can be calculated using A, which is a value related to the electromagnetic properties inside the subject and the distance between points inside the subject, and the background medium Green's function Ge. The reception Green's function and the transmission Green's function can be calculated using Equation 4 and Equation 5.

$$G(r_{Tx,1} \mid r_n) =$$ (Equation 4)

$$G_b(r_{Tx,1} \mid r_n) + k_b^2 \int_b G_b(r_m \mid r_n) v(r_m) G(r_{Tx,1} \mid r_m) ds(r_m)$$

$$G = A^{-1} G_b$$ (Equation 5)

Before treatment, the focusing parameter may be calculated according to breathing using Equation 1, Equation 2, and Equation 3. The focusing parameter may be calculated at that time using data received from the position and shape monitoring unit. In this case, the pre-calculated focusing parameter may correspond to a focusing parameter that does not take into account the influence of other normal tissues. The pre-calculated focusing parameter may correspond to an optimal focusing parameter calculated through an optimization process.

Figure 6:
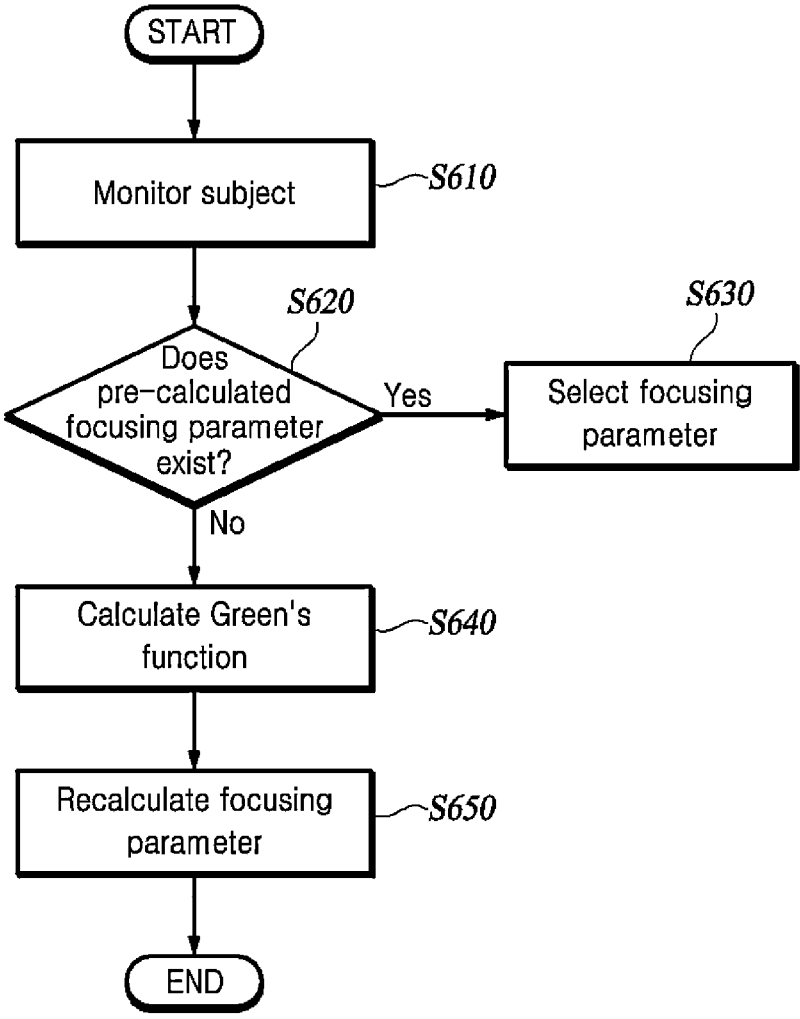
FIG. 6 is a diagram for explaining a process of calculating focus parameters during treatment, according to one embodiment of the present disclosure.

FIG. 6 is a diagram for explaining a process of calculating focus parameters during treatment, according to one embodiment of the present disclosure. For time points calculated before treatment, pre-calculated focusing parameters may be used. New focusing parameters need to be calculated for a new time point other than the time point calculated before treatment. In this case, the numerical model needed to calculate new focusing parameters may be obtained in real time using medical images such as MRI. The numerical model needed to calculate the new focusing parameter may be obtained using the numerical model at the time points before and after the new time point.

Referring to FIG. 6, the subject may be monitored (S610). The subject may be monitored by the position and shape monitoring unit. It may be determined whether there are pre-calculated parameters corresponding to a numerical model of the image received from the position and shape monitoring unit (S620). If a pre-calculated parameter exists (Yes in S620), a focusing parameter may be selected (S630). A target may be irradiated with radio wave energy using the selected focusing parameter. If no pre-calculated parameter exists (No in S620), the Green's function may be calculated (S640). If no pre-calculated parameter exists, the Green's function at a new time point may be calculated. This Green's function may be calculated using Equation 6.

$$G_n = A_n^{-1} G_b$$ (Equation 6)

$G_n$ may correspond to the Green's function at time $t_n$. The Green's function at a time point between time $t_n$ and time $t_{n+1}$ can be calculated using Equation 7.

$$G_{n+\Delta n} = A_{n+\Delta n}^{-1} G_b = (A_n + \Delta A)^{-1} G_b$$ (Equation 7)

Here, $(A_n + \Delta A)^{-1}$ can be expressed as Equation 8.

$$(A_n + \Delta A)^{-1} = A_n^{-1} - A_n^{-1} (A_n \Delta A^{-1} + 1)^{-1}$$ (Equation 8)

In this way, the Green's function can be calculated at any point in time. When the position of the subject changes independently of breathing, a new Green's function may be calculated. When the position of the subject changes, the value of A in Equation 5 may not change, and the background medium Green's function for each point of the subject may change. When the position of the subject changes, a new Green's function can be calculated using Equation 9.

$$G' = A^{-1} G_b'$$ (Equation 9)

A new Green's function can be calculated using $A^{-1}$ calculated in Equation 5 and the background medium Green's function $G_b'$ changed according to the change of position.

The focusing parameters may be recalculated using the calculated Green's function (S650). The electromagnetic properties may change depending on temperature changes in addition to the subject's breathing and changes in the subject's position. The Green's function may be calculated and the focusing parameter may be recalculated in consideration of the change in electromagnetic properties due to the temperature change.

Figure 7:
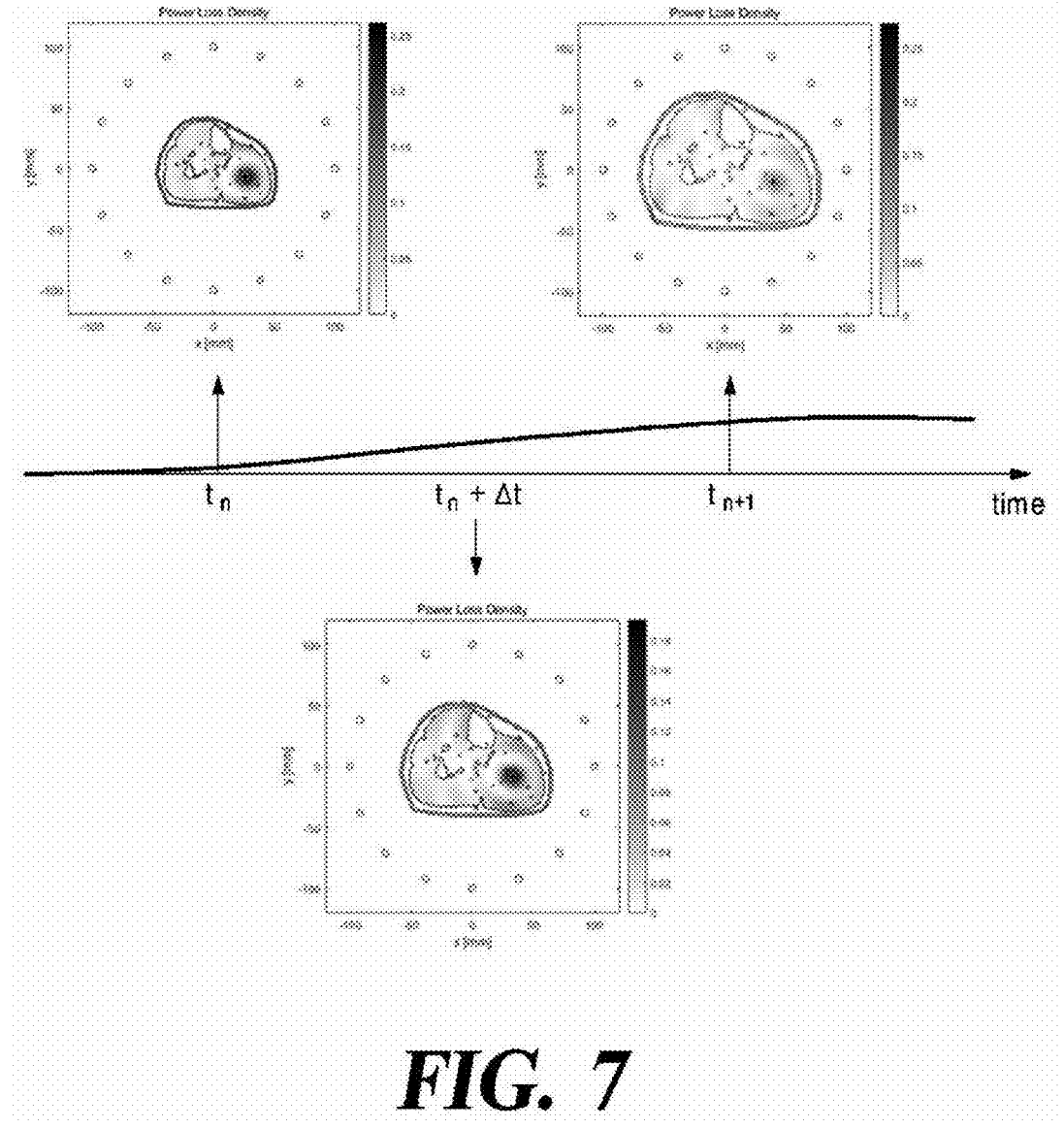
FIG. 7 is a diagram for explaining power loss density according to the breathing of a subject, according to one embodiment of the present disclosure.

FIG. 7 is a diagram for explaining power loss density according to the breathing of a subject, according to one embodiment of the present disclosure.

FIG. 7 shows the power loss density of the subject when the subject is breathing and the time is $t_1$. The position of the subject is displayed by the x-axis and y-axis in mm units. The power loss density for each position of the subject is displayed. Further, FIG. 7 shows the power loss density of the subject when a subject is breathing and the time is $t_n + \Delta t$. The position of the subject is displayed by the x-axis and y-axis in mm units. The power loss density for each position of the subject is displayed. In addition, FIG. 7 shows the power loss density of the subject when the subject is breathing and the time is $t_{n+1}$. The position of the subject is displayed by the x-axis and y-axis in mm units. The power loss density for each position of the subject is displayed. As the subject breathes, it can be seen that the size of the subject expands.

FIGS. 8A, 8B, 8C, 8D, 8E, and 8F are diagrams for explaining the power loss density and the phase of the focusing parameter according to the movement of the subject, according to one embodiment of the present disclosure.

Figure 8A:
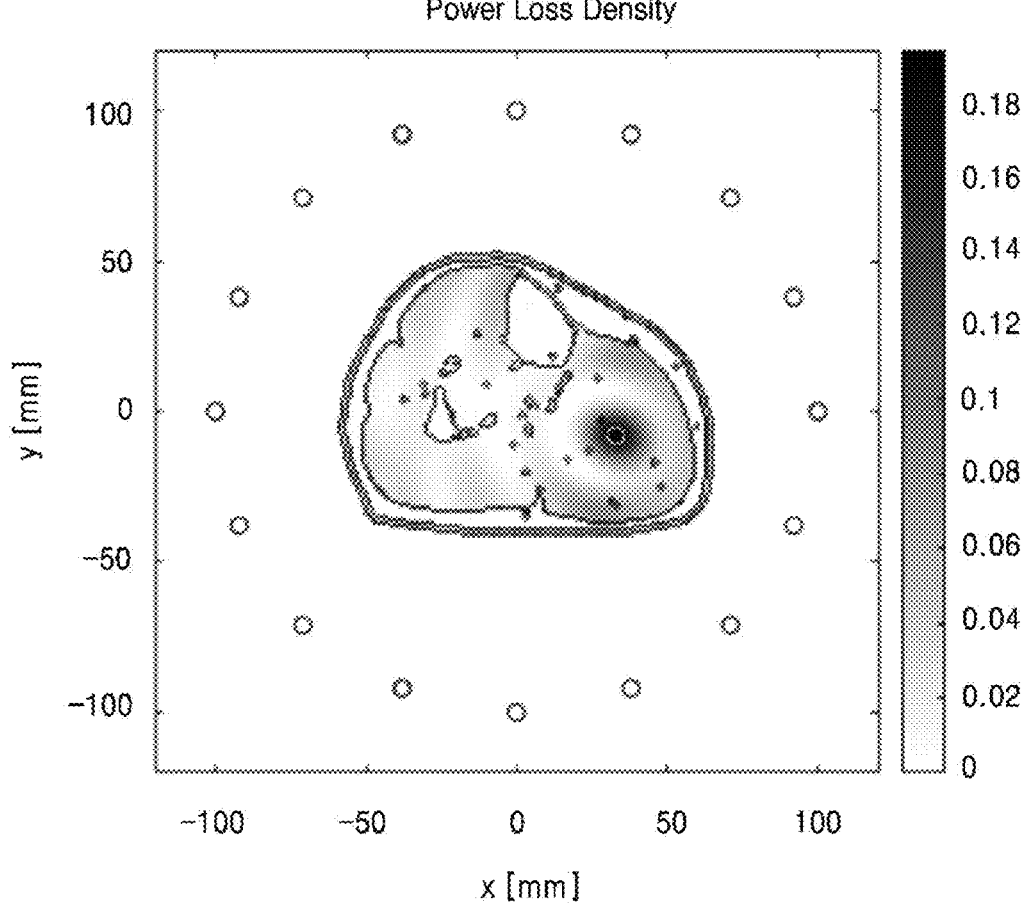
FIGS. 8A, 8B, 8C, 8D, 8E, and 8F are diagrams for explaining the power loss density and the phase of the focusing parameter according to the movement of the subject, according to one embodiment of the present disclosure.

FIG. 8A shows the power loss density of the subject in the initial state. The position of the subject is displayed by the x-axis and y-axis in mm units. The power loss density for each position of the subject is displayed.

Figure 8B:
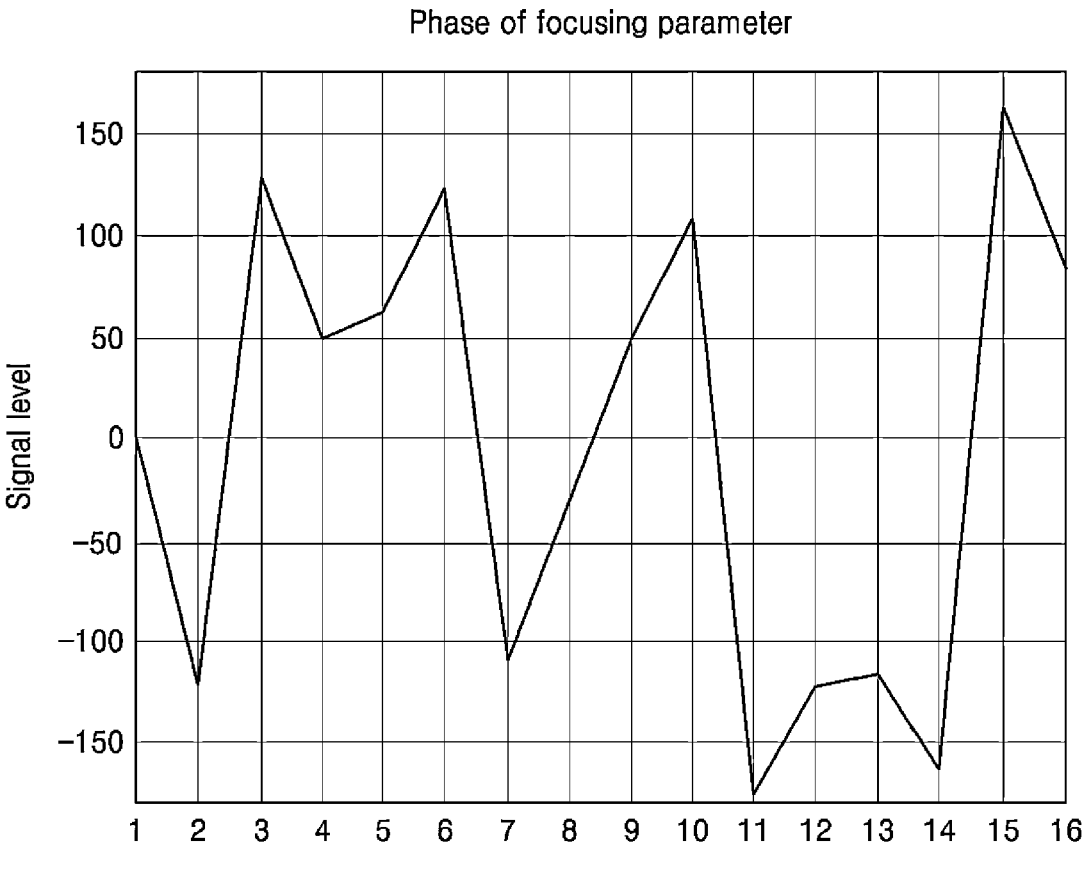

FIG. 8B shows the phase of the focusing parameter when the subject is in the initial state. The phase of the focusing parameter is displayed for each antenna. There are 16 antennas and they are identified by an index.

Figure 8C:
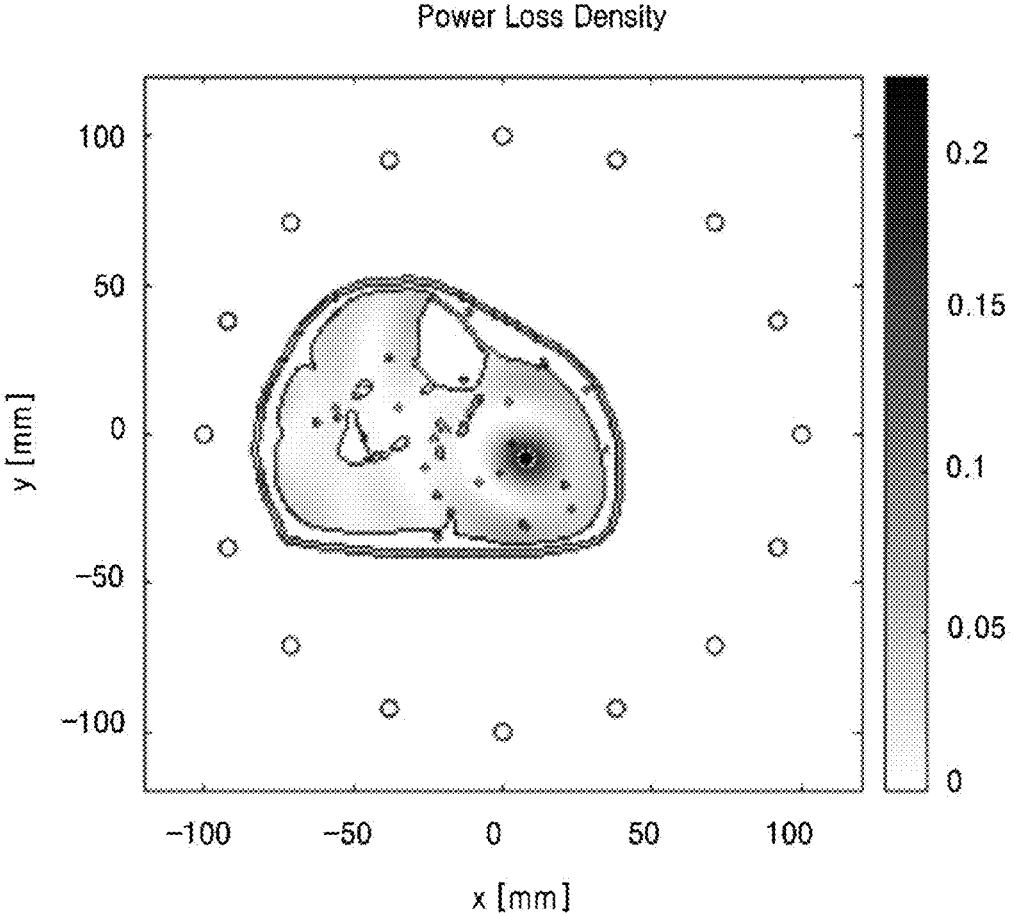

FIG. 8C shows the power loss density of the subject when the subject moves to the left from the initial state. The position of the subject is displayed by the x-axis and y-axis in mm units. The power loss density for each position of the subject is displayed.

Figure 8D:
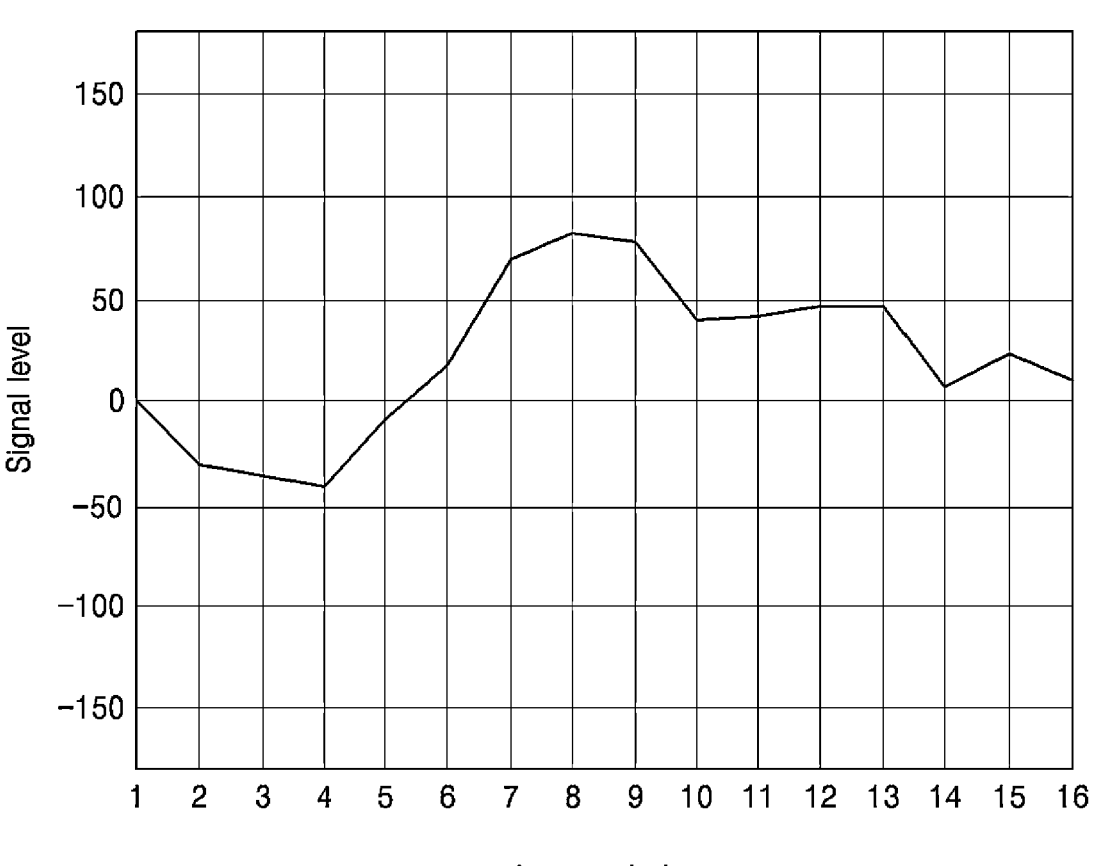

FIG. 8D shows the phase of the focusing parameter when the subject moves to the left from the initial state. The phase of the focusing parameter is displayed for each antenna. There are 16 antennas and they are identified by an index.

Figure 8E:
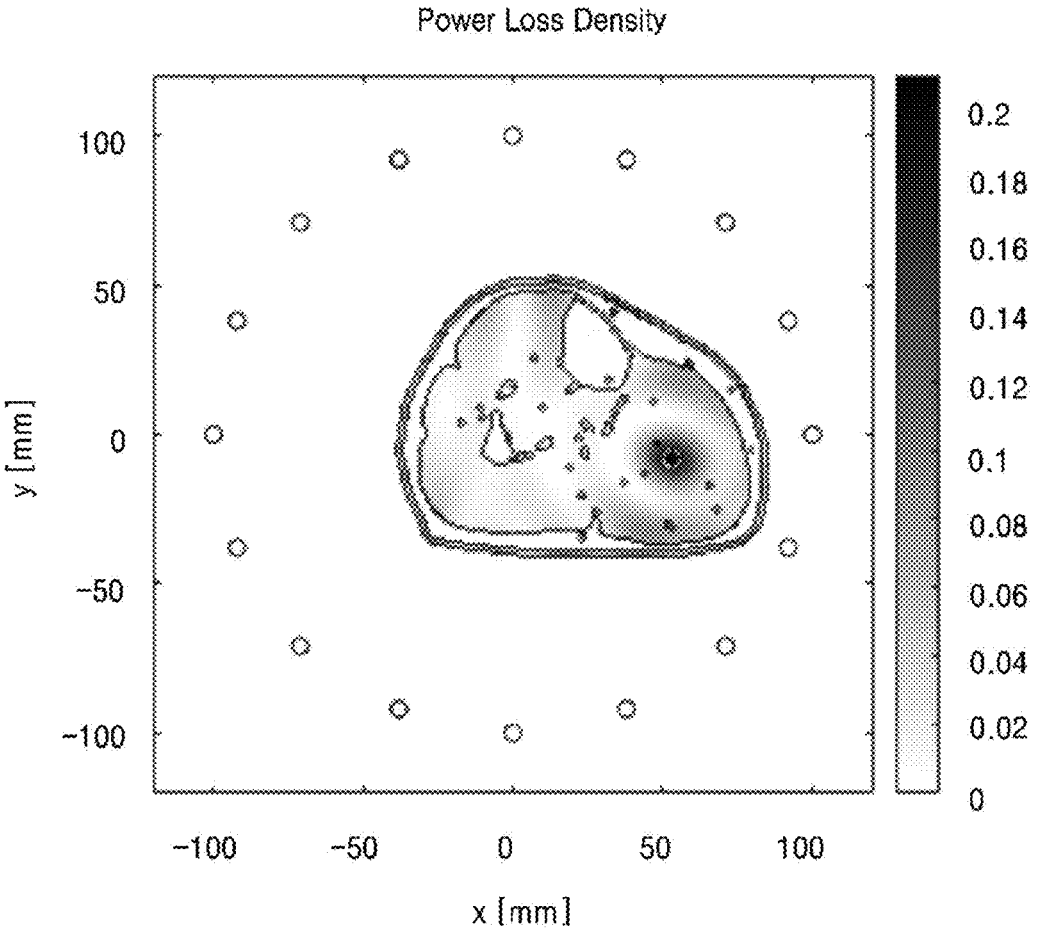

FIG. 8E shows the power loss density of the subject when the subject moves to the right from the initial state. The position of the subject is displayed by the x-axis and y-axis in mm units. The power loss density for each position of the subject is displayed.

Figure 8F:
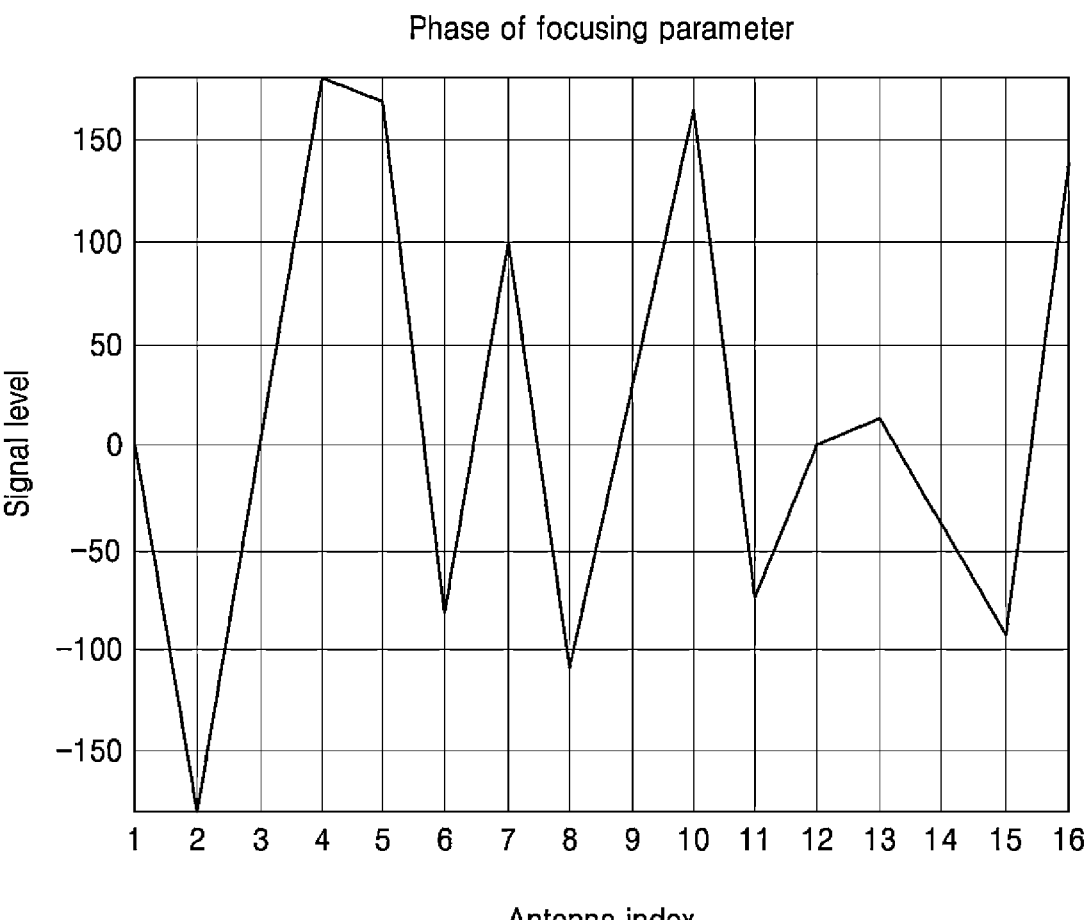

FIG. 8F shows the phase of the focusing parameter when the subject moves to the right from the initial state. The phase of the focusing parameter is displayed for each antenna. There are 16 antennas and they are identified by an index.

Figure 9:
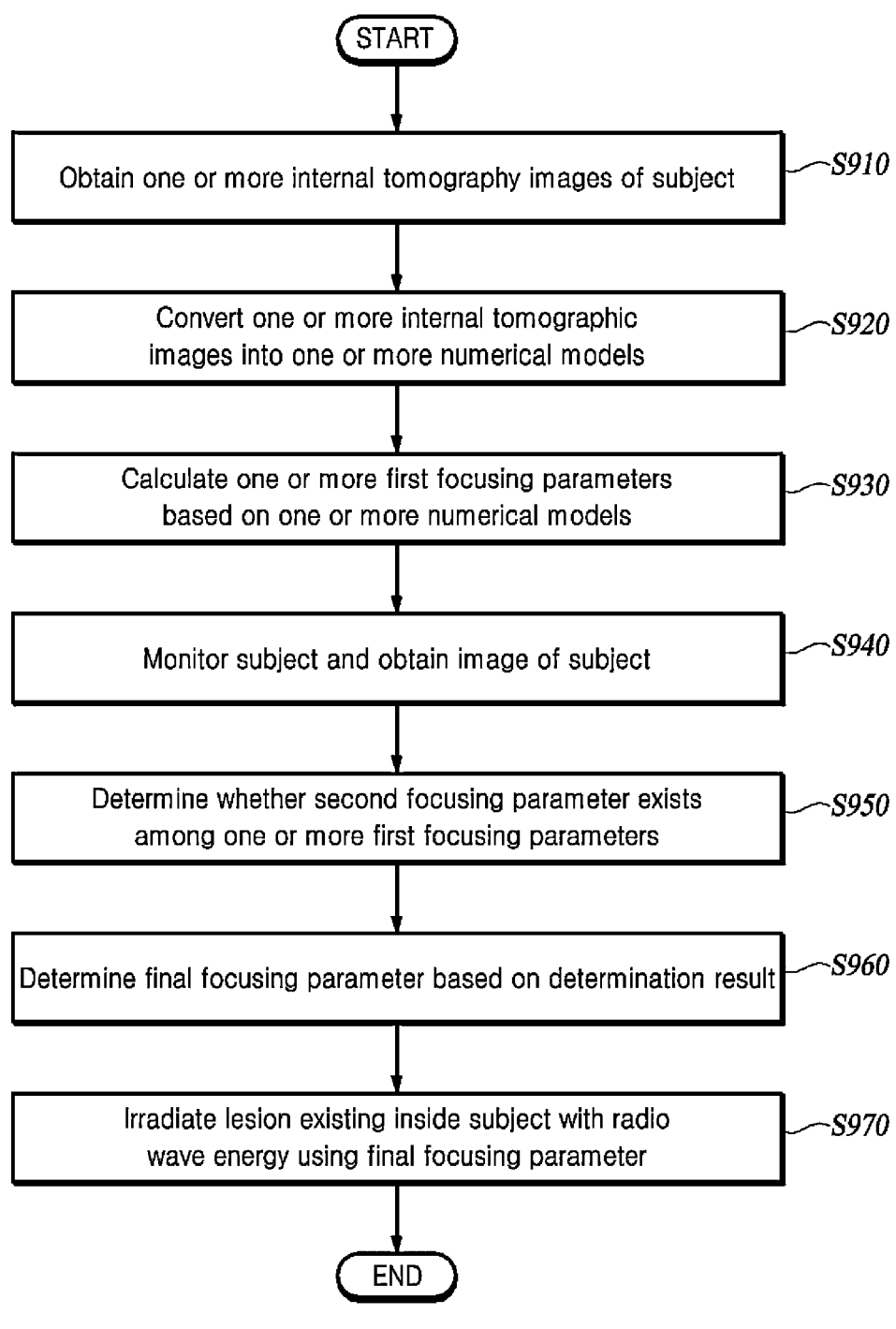
FIG. 9 is a diagram for explaining a method of focusing radio wave energy on a subject according to one embodiment of the present disclosure.

FIG. 9 is a diagram for explaining a method of focusing radio wave energy on a subject according to one embodiment of the present disclosure.

Referring to FIG. 9, an apparatus for focusing radio wave energy may obtain one or more internal tomography images of a subject (S910). The one or more internal tomographic images may correspond to time-specific internal tomographic images according to the subject's breathing. The apparatus for focusing radio wave energy may convert one or more internal tomographic images into one or more numerical models (S920). The apparatus for focusing radio wave energy may calculate one or more first focusing parameters based on the one or more numerical models (S930). The calculating of one or more first focusing parameters may include: calculating a transmission Green's function and a reception Green's function; calculating multi-state data using the transmission Green's function and the reception Green's function; decomposing the multi-state data into a plurality of singular values; and calculating one or more first focusing parameters based on the plurality of singular values. The one or more first focusing parameters may be calculated based on the first right singular vector among the plurality of singular values.

The apparatus for focusing radio wave energy may monitor the subject and obtain an image of the subject (S940). The image of a subject may be obtained based on at least one of an MRI imaging device, an electromagnetic wave sensor, a laser sensor, and a piezoelectric sensor. The apparatus for focusing radio wave energy may determine whether a second focusing parameter exists among the one or more first focusing parameters based on the image of the subject (S950). The apparatus for focusing radio wave energy may determine a final focusing parameter based on the determination result (S960). The determining of the final focusing parameter may include determining the second focusing parameter as the final focusing parameter when the second focusing parameter exists among the one or more first focusing parameters.

The determining of the final focusing parameter may include calculating a Green's function at the time when the image of the subject is monitored if the second focusing parameter does not exist among the one or more first focusing parameters, calculating the second focusing parameter using the Green's function, and determining the second focusing parameter as the final focusing parameter.

The determining of the final focusing parameter includes, when no second focusing parameter exists among the one or more first focusing parameters and the position of the subject changes, calculating a Green's function using the background medium Green's function according to the change in the position of the subject, calculating a second focusing parameter using the Green's function, and determining the second focusing parameter as the final focusing parameter.

The determining of the final focusing parameter includes, when no second focusing parameter exists among the one or more first focusing parameters and the temperature of the subject changes, calculating a Green's function using the temperature of the subject, calculating a second focusing parameter using the Green's function, and determining the second focusing parameter as the final focusing parameter.

The apparatus for focusing radio wave energy may irradiate a lesion existing inside the subject with radio wave energy using the final focusing parameter (S970). The radio wave energy may be radiated through a plurality of antennas. The plurality of antennas may be comprised of multiple layers.

Each element of the apparatus or method in accordance with the present invention may be implemented in hardware or software, or a combination of hardware and software. The functions of the respective elements may be implemented in software, and a microprocessor may be implemented to execute the software functions corresponding to the respective elements.

Various embodiments of systems and techniques described herein can be realized with digital electronic circuits, integrated circuits, field programmable gate arrays (FPGAs), application specific integrated circuits (ASICs), computer hardware, firmware, software, and/or combinations thereof. The various embodiments can include implementation with one or more computer programs that are executable on a programmable system. The programmable system includes at least one programmable processor, which may be a special purpose processor or a general purpose processor, coupled to receive and transmit data and instructions from and to a storage system, at least one input device, and at least one output device. Computer programs (also known as programs, software, software applications, or code) include instructions for a programmable processor and are stored in a "computer-readable recording medium."

The computer-readable recording medium may include all types of storage devices on which computer-readable data can be stored. The computer-readable recording medium may be a non-volatile or non-transitory medium such as a read-only memory (ROM), a random access memory (RAM), a compact disc ROM (CD-ROM), magnetic tape, a floppy disk, or an optical data storage device. In addition, the computer-readable recording medium may further include a transitory medium such as a data transmission medium. Furthermore, the computer-readable recording medium may be distributed over computer systems connected through a network, and computer-readable program code can be stored and executed in a distributive manner.

Although operations are illustrated in the flowcharts/ timing charts in this specification as being sequentially performed, this is merely an exemplary description of the technical idea of one embodiment of the present disclosure. In other words, those skilled in the art to which one embodiment of the present disclosure belongs may appreciate that various modifications and changes can be made without departing from essential features of an embodiment of the present disclosure, that is, the sequence illustrated in the flowcharts/timing charts can be changed and one or more operations of the operations can be performed in parallel. Thus, flowcharts/timing charts are not limited to the temporal order.

Although exemplary embodiments of the present disclosure have been described for illustrative purposes, those skilled in the art will appreciate that various modifications, additions, and substitutions are possible, without departing from the idea and scope of the claimed invention. Therefore, exemplary embodiments of the present disclosure have been described for the sake of brevity and clarity. The scope of the technical idea of the present embodiments is not limited by the illustrations. Accordingly, one of ordinary skill would understand that the scope of the claimed invention is not to be limited by the above explicitly described embodiments but by the claims and equivalents thereof.

What is claimed is:

1. A method performed by an apparatus for focusing radio wave energy, the method comprising:

obtaining one or more internal tomographic images of a subject;

converting the one or more internal tomographic images into one or more numerical models;

calculating one or more first focusing parameters based on the one or more numerical models;

obtaining an image of the subject by monitoring the subject;

determining whether a second focusing parameter exists among the one or more first focusing parameters based on the image of the subject;

determining a final focusing parameter based on the determination result; and irradiating a lesion existing inside the subject with the radio wave energy using the final focusing parameter, wherein the radio wave energy is radiated through a plurality of antennas.

2. The method of claim 1, wherein the one or more internal tomographic images correspond to time-specific internal tomographic images according to breathing of the subject.

3. The method of claim 1, wherein calculating the one or more first focusing parameters comprises:

calculating a transmission Green's function and a reception Green's function;

calculating multi-state data using the transmission Green's function and the reception Green's function;

decomposing the multi-state data into a plurality of singular values; and calculating the one or more first focusing parameters based on the plurality of singular values.

4. The method of claim 3, wherein the one or more first focusing parameters are calculated based on a first right singular vector among the plurality of singular values.

5. The method of claim 1, wherein the image of the subject is obtained based on at least one of an MRI imaging device, an electromagnetic wave sensor, a laser sensor, and a piezoelectric sensor.

6. The method of claim 1, wherein determining the final focusing parameter comprises:

determining the second focusing parameter as the final focusing parameter when the second focusing parameter exists among the one or more first focusing parameters.

7. The method of claim 1, wherein determining the final focusing parameter comprises:

when the second focusing parameter does not exist among the one or more first focusing parameters, calculating a Green's function at a time when the image of the subject is monitored;

calculating the second focusing parameter using the Green's function; and determining the second focusing parameter as the final focusing parameter.

8. The method of claim 1, wherein determining the final focusing parameter comprises:

when the second focusing parameter does not exist among the one or more first focusing parameters and a position of the subject changes, calculating a Green's function using a background medium Green's function according to the change in the position of the subject;

calculating the second focusing parameter using the Green's function; and determining the second focusing parameter as the final focusing parameter.

9. The method of claim 1, wherein determining the final focusing parameter comprises:

when the second focusing parameter does not exist among the one or more first focusing parameters and a temperature of the subject changes, calculating a Green's function using the temperature of the subject;

calculating the second focusing parameter using the Green's function; and determining the second focusing parameter as the final focusing parameter.

10. The method of claim 1, wherein the plurality of antennas are arranged in multiple layers.

11. An apparatus for focusing radio wave energy, comprising:

a memory; and a plurality of processors, wherein at least one processor among the plurality of processors is configured to:

obtain one or more internal tomographic images of a subject, convert the one or more internal tomographic images into one or more numerical models, calculate one or more first focusing parameters based on the one or more numerical models, obtain an image of the subject by monitoring the subject, determine whether a second focusing parameter exists among the one or more first focusing parameters based on the image of the subject, determine a final focusing parameter based on the determination result, and irradiate a lesion existing inside the subject with the radio wave energy to using the final focusing parameter, wherein the radio wave energy is radiated through a plurality of antennas, and wherein the plurality of antennas are arranged in multiple layers.

12. The apparatus of claim 11, wherein the one or more internal tomographic images correspond to time-specific internal tomographic images according to breathing of the subject.

13. The apparatus of claim 11, wherein the at least one processor is further configured to:

calculate a transmission Green's function and a reception Green's function;

calculate multi-state data using the transmission Green's function and the reception Green's function;

decompose the multi-state data into a plurality of singular values; and calculate the one or more first focusing parameters based on the plurality of singular values.

14. The apparatus of claim 13, wherein the one or more first focusing parameters are calculated based on a first right singular vector among the plurality of singular values.

15. The apparatus of claim 11, wherein the image of the subject is obtained based on at least one of an MRI imaging device, an electromagnetic wave sensor, a laser sensor, and a piezoelectric sensor.

16. The apparatus of claim 11, wherein the at least one processor is further configured to:

determine the second focusing parameter as the final focusing parameter when the second focusing parameter exists among the one or more first focusing parameters.

17. The apparatus of claim 11, wherein when the second focusing parameter does not exist among the one or more first focusing parameters, the at least one processor is further configured to:

calculate a Green's function at a time when the image of the subject is monitored, calculate the second focusing parameter using the Green's function, determine the second focusing parameter as the final focusing parameter.

18. The apparatus of claim 11, wherein when the second focusing parameter does not exist among the one or more first focusing parameters and a position of the subject changes, the at least one processor is further configured to:

calculate a Green's function using a background medium Green's function according to the change in the position of the subject, calculate the second focusing parameter using the Green's function, determine the second focusing parameter as the final focusing parameter.

19. The apparatus of claim 11, wherein when the second focusing parameter does not exist among the one or more first focusing parameters and a temperature of the subject changes, the at least one processor is further configured to:

calculating a Green's function using the temperature of the subject, calculating the second focusing parameter using the Green's function, determining the second focusing parameter as the final focusing parameter.

20. A computer-readable recording medium storing instructions, wherein the instructions, when executed by a computer, cause the computer to perform:

obtaining one or more internal tomographic images of a subject;

converting the one or more internal tomographic images into one or more numerical models;

calculating one or more first focusing parameters based on the one or more numerical models;

obtaining an image of the subject by monitoring the subject;

determining whether a second focusing parameter exists among the one or more first focusing parameters based on the image of the subject;

determining a final focusing parameter based on the determination result; and irradiating a lesion existing inside the subject with the radio wave energy to using the final focusing parameter, wherein the radio wave energy is radiated through a plurality of antennas.

* * * * *